US00PP16252P3

(12) United States Plant Patent
Carruth

(10) Patent No.: US PP16,252 P3
(45) Date of Patent: Feb. 14, 2006

(54) SHRUB ROSE PLANT NAMED 'WEKSACSOUL'

(50) Latin Name: *Rosa hybrida*
Varietal Denomination: WEKsacsoul

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 258 days.

(21) Appl. No.: 10/686,748

(22) Filed: Oct. 15, 2003

(65) Prior Publication Data

US 2005/0091718 P1 Apr. 28, 2005

(51) Int. Cl.
*A01H 5/00* (2006.01)

(52) U.S. Cl. ..... Plt./102

(58) Field of Classification Search ..... Plt./102, Plt./104, 107, 108, 130, 131, 132, 141, 142, Plt./143

See application file for complete search history.

*Primary Examiner*—Howard J. Locker
(74) *Attorney, Agent, or Firm*—Christie, Parker & Hale, LLP

(57) ABSTRACT

A new variety of Shrub rose suitable for garden decoration, having flowers of cerise coloration with a yellow center.

1 Drawing Sheet

Classification: The present invention relates to a new *Rosa hybrida* plant.

Variety denomination: The new plant has the varietal denomination 'WEKsacsoul'.

BACKGROUND OF THE INVENTION

This invention relates to a new and distinct variety of Shrub Rose. It has as its seed parent the variety known as 'POUlclaus' (U.S. Plant Pat. No. 9,063) and as its pollen parent an undisseminated seedling of my creation.

SUMMARY OF THE INVENTION

Among the features which distinguish the new variety from other presently available and commercial rose cultivars known to the inventor are the following combination of characteristics: its many stipitate glands on the peduncle and the bud surface, its suffusion of red pigment on the rachis and the stipule, its large clusters of single petaled flowers with moderately large yellow zones at the petal base and its inwardly reflexed petal edges. The plant has a bushy moderately spreading medium height growth habit suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsacsoul' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, 'POUlclaus' by the following combination of characteristics: whereas 'WEKsacsoul' bears medium sized flowers (about 5.2 to about 7.9 cm. in diameter) of cerise coloration with a yellow center, 'POUlclaus' bears smaller flowers (about 5.0 to about 6.5 cm. in diameter) of deep red coloration. 'WEKsausoul' bears flowers of single petalage (about 5 to 6 petals), whereas 'POUlclaus' bears flowers of significantly heavier petalage (about 14 to 18 petals). The new variety has a bushy moderately spreading medium height growing habit, whereas the seed parent has a significantly smaller bushy upright mature growing habit.

The new variety may be distinguished from its pollen parent, an undisseminated seedling of my creation by the following combination of characteristics: whereas 'WEKsacsoul' bears flowers of cerise coloration with a yellow center, the undisseminated seedling bears flowers of pale yellow coloration. The new variety is classified as a shrub rose with a bushy moderately spreading medium height growing habit, whereas the pollen parent is a climbing rose with a significantly taller and more spreading mature growing habit. 'WEKsacsoul' bears medium green moderately glossy foliage, whereas the pollen parent bears significantly darker very glossy foliage.

BRIEF DESCRIPTION OF THE ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety usually bears its flowers in clusters of five or more per stem. Flowers are borne in regular rounded to somewhat pyramidal clusters on strong medium stems (about 28 to about 82 cm.) Outdoors, the plant blooms abundantly and nearly continuously during the growing season. The flowers have a slight tea fragrance.

BUD

The peduncle is about 1.6 to about 3.6 cm. in length, of slender to average caliper (about 0.15 to about 0.2 cm. in diameter), and usually erect. It is moderately smooth, with many stipitate glands and few hairs. Peduncle color is between 144B and 147B sometimes lightly suffused, especially on the side exposed to the sun, with near 183C.

Before the calyx breaks, the bud is about 0.7 to 1.1 cm. in diameter at the widest point, about 1.0 to about 1.7 cm. in length, and pointed to somewhat ovoid in shape. The surface of the bud bears some foliaceous appendages and many stipitate glands, usually with slender somewhat cut foliaceous parts extending beyond the tip of the bud about ½ or more of its length. Bud color is between 144A and 147B sometimes moderately suffused, especially on the side exposed to the sun, with between 183C and 187A.

The sepals are about 1.6 to about 2.6 cm. in length and about 0.5 to about 0.7 cm. in width at the widest point. The outer surface color of the sepal is between 144A and 147B sometimes moderately suffused, especially on the side exposed to the sun, with between 183C and 187A. The inner surface color of the sepal is between 138B and 137B and covered with fine wooly tomentum; sepal margins are lined with many stipitate glands and few hairs.

As the petals often (after the clayx breaks), the bud is about 1.1 to about 1.6 cm. in diameter at the widest point, about 1.6 to about 2.1 cm. in length, and pointed to moderately ovoid in form. The color of the under surfaces of the newly opened petals is between 13C and 13B. At the point where the petal attaches, there is a moderately large zone of between 6C and 12C. The color of the upper surfaces of the newly opened petals is between 53A and 46A. At the point where the petal attaches, there is a moderately large zone of between 6B and 7C.

BLOOM

When fully open, the bloom ranges from about 5.2 to about 7.9 cm. in diameter. Petalage is single with about 5 to 6 petals and about 1 to 2 petaloids irregularly arranged. When partially open, the bloom form is very cupped to somewhat globular, and the petals are moderately cupped to somewhat undulated with petal edges moderately reflexed inward. When fully open, the bloom form is moderately cupped, and the petals are loosely cupped to somewhat undulated with petal edges somewhat reflexed inward.

PETALS

The substance of the petals is moderately heavy to somewhat leathery and of medium thickness, with upper surfaces slightly shiny to moderately satiny and under surfaces somewhat shiny to matte. The petals are broadly obovate in shape with rounded apices. The petals are about 2.5 to about 3.7 cm. in length and about 2.1 to about 3.4 cm. in width at the widest point. Petal margins are entire.

NEWLY OPENED FLOWER

The under surface color of the petals is between 11C and 12C. At the point where the petal attaches, there is a moderately large zone of between 6D and 12C. The upper surface color of the petals is between 52A and 45A. At the point where the petal attaches, there is a moderately large zone of between 6D and 7D.

The general tonality of the newly opened flower is between 52A and 45A with a moderately large zone at the base of the petals of between 6D and 7D.

THREE-DAY-OLD FLOWER

The under surface color of the petals is between 56D and 58D sometimes blushed with between 61B and 63A. There is no visible change in coloration at the point where the petal attaches. The upper surface color of the petals is between 57A and 53B. At the point where the petal attaches, there is a moderately large zone of between 155A and 155D usually blushed with between 61B and 63A.

The general tonality of the three-day-old flower is between 57A and 53B.

On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 125) and are arranged regularly about the pistils; a few are mixed with petaloids. The filaments are of somewhat short to medium length (about 0.4 to about 0.8 cm.), most with anthers. Filaments are between 9B and 12B in color. The anthers are somewhat small to medium for the class and all open approximately at the same time. Anther color is between 24B and 171C when immature and between 164D and 200C at maturity. Pollen is abundant.

FEMALE REPRODUCTIVE ORGANS

Pistils vary in number (average about 35). The styles are very even, average in length (about 0.5 to about 0.7 cm.), somewhat thin to average in caliper, and loosely bunched. Stigma color is between 8B and 10B. Style color is between 1D and 2D often lightly suffused near the top with between 53C and 53D. Ovaries are usually all enclosed in the calyx.

Hips are of somewhat long length (about 5.1 to about 2.8 cm.), moderately rounded to somewhat obovate in form, and between 25A and 28B in color when ripe. The hip surface is very smooth with thick fleshy walls. The sepals are moderately permanent, somewhat long in length, and usually straight in shape. The seeds are irregularly rounded, smooth in texture, approximately 4 to about 13 per hip, about 0.3 to about 0.5 cm. in diameter at the widest point and between 160C and 162C in color.

FOLIAGE

The compound leaves are usually comprised of three to seven or more leaflets and are borne abundantly. The seven-leaflet leaves are about 9.1 to about 12.9 cm. in length and about 7.1 to about 9.9 cm. in width at the widest point, moderately leathery to slightly crisp in texture, and moderately glossy in finish. The terminal leaflets are about 3.9 to about 6.1 cm. in length and about 1.9 to about 4.2 cm. in width at the widest point, shaped moderately ovate to somewhat oval with moderately acuminate apices and rounded bases. Their margins are usually simply serrate.

The upper surface color of the mature leaf is between 147A and 137C. The under surface color of the mature leaf is between 137B and 148B. The upper surface color of the young leaf is between 137C and 144B, sometimes lightly suffused between 187A and 183A. The under surface color of the young leaf is between 138B and 148B, sometimes heavily suffused with between 187B and 183A.

The rachis is average in caliper and moderately rough. The upper side is shallowly grooved with very few hairs and many stipitate glands on the edges of the grooves. The under side of the rachis is moderately rough with some stipitate glands and small prickles. The rachis color is between 145B and 144C sometimes heavily suffused on the upper side with between 187A and 187B.

The stipules are about 1.1 to about 1.5 cm. in length and moderately wide (about 0.5 to about 0.7 cm.) with somewhat long straight points that usually turn out an angle of more than 45 degrees and sometimes recurve toward the stem. The stipules color is between 137A and 138A sometimes heavily suffused with between 187A and 187B.

The petiole is about 0.3 to about 1.1 cm. in length and about 0.15 to about 0.2 cm in diameter at the widest point. The petiole color is between 145B and 144C sometimes heavily suffused on the upper side with between 187A and 187B.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a bushy moderately spreading medium height growth habit (about 77 to about 108 cm. in height and about 108 to about 121 cm. spread at the widest point), with full branching. It displays moderately vigorous growth and the canes are of somewhat light to medium caliper for the class.

The color of the major stems is between 146A and 146B. They bear many large prickles that are about 0.6 to about 1.1 cm. in length. The large prickles are slightly hooked downward with a somewhat short to medium length moderately broad oval base; prickle color is between 166D and 173D. The major stem bears few small prickles of similar shape and coloration.

The color of the branches is between 144A and 147B. They bear some large prickles which are of similar size and shape to the large prickles on the major stems; prickle color is between 145C and 145B sometimes lightly suffused with between 187B and 184B. The branches bear very few small prickles of similar shape and coloration.

The color of the new shoots is between 146B and 147B often moderately suffused with between 187B and 183A. They bear some large prickles which are of similar size and shape to the large prickles on the major stems; prickle color is between 145C and 145B sometimes lightly suffused with between 187B and 184B. The shoots bear very few small prickles of similar shape and coloration.

I claim:

1. A new and distinct shrub rose plant of the variety substantially as described and illustrated herein.

* * * * *

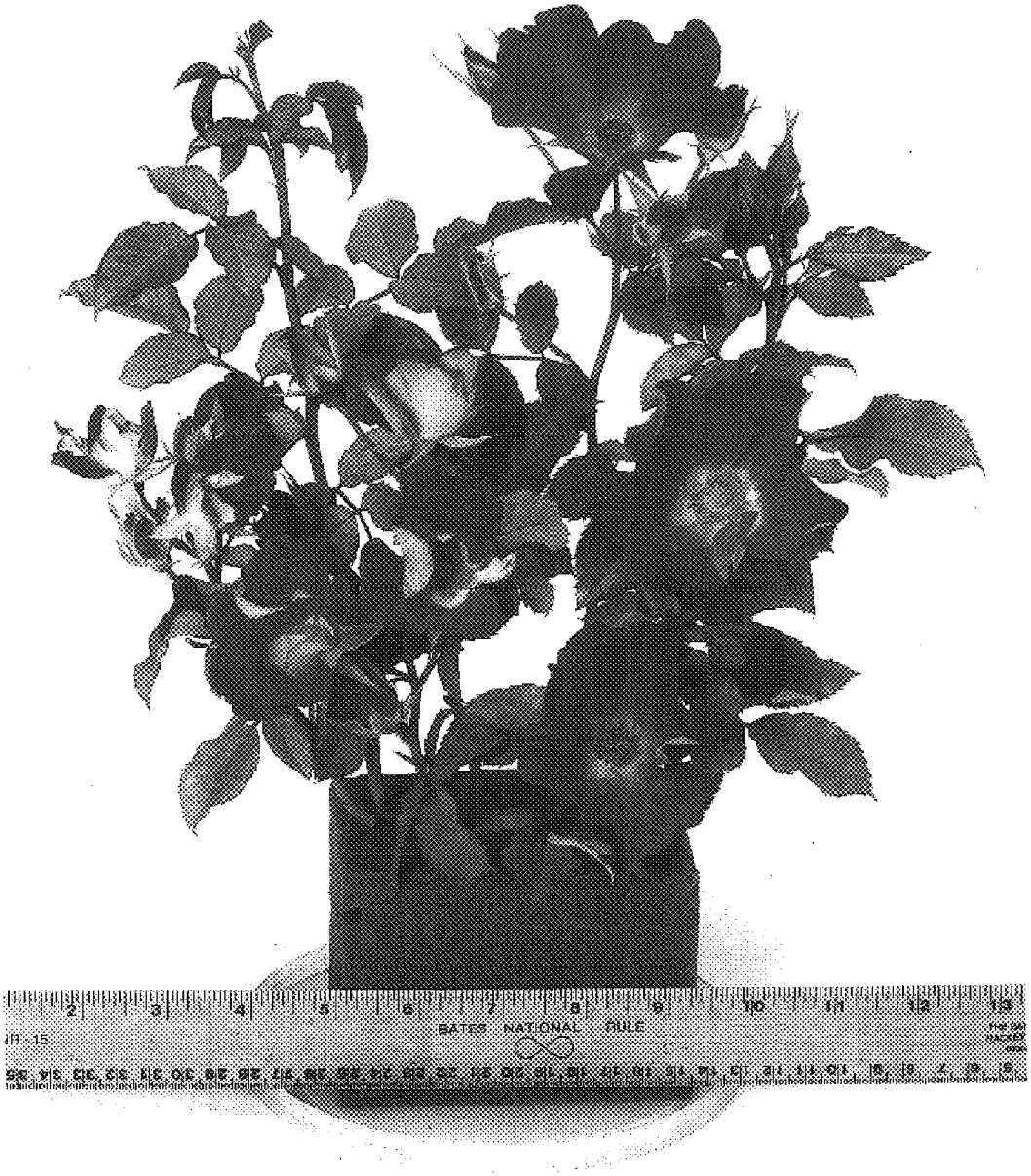
BATES NATIONAL RULE